US008275835B2

(12) United States Patent
Eguchi (10) Patent No.: US 8,275,835 B2
(45) Date of Patent: Sep. 25, 2012

(54) RADIOGRAPHIC IMAGE CAPTURING SYSTEM

(75) Inventor: Yoshihiko Eguchi, Tokorozawa (JP)

(73) Assignee: Konica Minolta Medical & Graphic, Inc. (JP)

( * ) Notice: Subject to any disclaimer, the term of this patent is extended or adjusted under 35 U.S.C. 154(b) by 234 days.

(21) Appl. No.: 12/676,172

(22) PCT Filed: Aug. 21, 2008

(86) PCT No.: PCT/JP2008/064894
§ 371 (c)(1),
(2), (4) Date: Mar. 3, 2010

(87) PCT Pub. No.: WO2009/031411
PCT Pub. Date: Mar. 12, 2009

(65) Prior Publication Data
US 2010/0169423 A1     Jul. 1, 2010

(30) Foreign Application Priority Data
Sep. 6, 2007   (JP) ................................ 2007-231258

(51) Int. Cl.
G06F 15/16 (2006.01)
H01J 31/49 (2006.01)
A61B 5/00 (2006.01)
(52) U.S. Cl. .......................... 709/204; 378/189; 600/300
(58) Field of Classification Search .................. 709/204; 600/300; 378/189
See application file for complete search history.

(56) References Cited

U.S. PATENT DOCUMENTS

| 6,795,572 | B1 | 9/2004 | Matsuno | |
| 7,197,112 | B2 * | 3/2007 | Maschke | 378/91 |
| 7,446,318 | B2 * | 11/2008 | Campbell | 250/368 |
| 2004/0114725 | A1 * | 6/2004 | Yamamoto | 378/189 |
| 2006/0080143 | A1 | 4/2006 | Tsuchino et al. | |
| 2006/0094936 | A1 * | 5/2006 | Russ | 600/300 |
| 2008/0049901 | A1 * | 2/2008 | Tamakoshi | 378/98.2 |
| 2010/0104065 | A1 * | 4/2010 | Eguchi | 378/62 |

FOREIGN PATENT DOCUMENTS

| JP | 2001-37749 A | 2/2001 |
| JP | 2003-169061 A | 6/2003 |
| JP | 2004-180931 A | 7/2004 |
| JP | 2006-247141 A | 9/2006 |
| WO | 2005/096944 A1 | 10/2005 |
| WO | 2006/033220 A1 | 3/2006 |
| WO | 2006/109551 A1 | 10/2006 |

OTHER PUBLICATIONS

International Search Report for International Application No. PCT/JP2008/064894 mailed Sep. 22, 2008 with English Translation.

* cited by examiner

Primary Examiner — Asghar Bilgrami
(74) Attorney, Agent, or Firm — Cantor Colburn LLP (57) ABSTRACT

Disclosed is a radiographic image capturing system, in which a portable-type radiographic image detecting device provided with a wireless communication section is included, and a correlation established between the FPD and the console can be easily changed. The system further includes a plurality of controlling terminal devices, each of which displays a radiation image; a communication information attaching section to attach communication information to the radiation image data; an access point that is correlated with corresponding one of the controlling terminal devices, and transfers the radiation image data, which is received by the wireless communication section in the wireless communication mode within a predetermined area of a radiographing room, into the network; and a correlation controlling section that correlates the radiographic image detecting device with the corresponding one of the controlling terminal devices so as to establish a correlation establishment between them, based on the communication information.

6 Claims, 8 Drawing Sheets

RADIOGRAPHIC IMAGE CAPTURING SYSTEM

This is a U.S. national stage application of International Application No. PCT/JP2008/064894, filed on 21 Aug. 2008. Priority under 35 U.S.C. §119(a) and 35 U.S.C. §365(b) is claimed from Japanese Application No. 2007-231258, filed Sep. 6, 2007, the disclosure of which is also incorporated herein by reference.

FIELD OF THE INVENTION

The present invention relates to a radiographic image capturing system, and specifically relates to such a radiographic image capturing system that employs a potable-type radiographic image detecting device having a wireless communication capability.

TECHNICAL BACKGROUND

In recent years, a digitalized radiographic image detecting device has been employed as a method for acquiring a radiographic image, including the processes of irradiating radial rays onto a subject and detecting radial rays penetrated through the subject. For this purpose, so-called FPD (Flat Panel Detector) can be employed for the radiographic image detecting device above-mentioned.

For instance, a certain FPD is so constituted that a plurality of detecting elements are two-dimensionally aligned on a substrate, and radial rays penetrated through the subject are irradiated onto a phosphor member (scintillator), and then, each of the plurality of detecting elements converts the intensity of visible light, generated corresponding to the amount of radial rays irradiated, to an amount of electric charge to be stored in a capacitor, so as to acquire the radiographic image by reading out the electric charges stored in the capacitors. The abovementioned FPD has such immediacy that the concerned radiographic image can be obtained just after the radiographic image capturing operation is completed.

Further, the recent advancement of the semiconductor manufacturing technology makes the dimensions of the FPD minimized and thinned. Still further, Tokkai 2004-180931 (Japanese Patent Application Laid-Open Publication) sets forth an X-ray image capturing apparatus that is provided with such the thin-type FPD and a communication device having a wireless communication capability.

On the other hand, from the viewpoints of making the information utility convenient and speeding up various kinds of processing, the HIS (Hospital Information System) serving as such a system that totally controls patient diagnosis information and accounting information, the RIS (Radiology Information System) serving as such a system that controls the image capturing orders to be conducted in the department of radiology, etc., have been introduced into the hospital. In such the system, various kinds of radiographic image capturing apparatuses and terminal devices for controlling the capturing apparatuses, etc., are coupled to the RIS or the HIS through a network installed in the hospital, such as LAN (Local Area Network), etc.

Further, International Publication 06/109551 sets forth a radiographic image capturing system in which both a plurality of consoles (each serving as a controlling terminal device) and a plurality of FPDs (each being provided with a communication function) are coupled to the above-mentioned network installed in the hospital. According to the radiographic image capturing system set forth in International Publication 06/109551, in order to improve an efficiency of image confirming operations to be conducted by various kinds of operators, such as a radiologist, a doctor, etc., the plurality of consoles and the plurality of FPDs are correlated with each other in advance, so as to transmit the radiographic image, acquired by a specific FPD, to the console correlated to the specific FPD in advance.

Still further, International Publication 05/096944 sets forth another radiographic image capturing system in which a plurality of consoles and a plurality of FPDs, each of which is a portable cassette-type FPD (hereinafter, also referred to as a portable-type FPD) provided with a wireless communication section, are coupled to each other by using a radio repeater installed in the image capturing room. According to the radiographic image capturing system set forth in International Publication 05/096944, when the radiographing operation is implemented by employing the FPD, an ID (Identification) of the operator who conducts the radiographing operation concerned is correlated to the captured image data. Then, when operating the console that displays the radiographic image acquired by implementing the radiographing operation concerned thereon, the concerned radiographer registers the operator's ID, while the FPD transmits the image data, correlated with an operator's ID coinciding with that registered by the concerned radiographer, to the console concerned. By employing the above-mentioned method, even when the radiographer repeats the radiographing operations while moving from one to another console among the plurality of consoles, it becomes possible for the radiographer to confirm the radiographic images, represented by the image data acquired by the radiographing operations, at a specific console which is currently used by the radiographer concerned, resulting in improvement of the efficiency of the radiographing operations.

As for the radiographic image capturing system set forth in Patent Document 2 or Patent Document 3, it is necessary to correlate the FPD with the console installed in the radiographing room in advance when the radiographing operation is actually implemented.

Other than the purpose of improving the efficiency of image confirming operation, the reason why the FPD is correlated with the console lays on such purposes that, by storing radiographing sensitivity information in advance into the console correlated, the image correcting operation is speedily performed and the operation in regard to the timing of image capturing operation is synchronized with the X-ray generating apparatus to be used for the radiographing operation concerned.

However, sometimes, the portable-type FPD provided with the wireless communication section is used by moving it between plural radiographing rooms. For instance, in case that a FPD, singly installed in a certain radiographing room, has malfunctioned and another FPD is moved to the concerned radiographing room from another radiographing room so as to backup the malfunctioned FPD, due to such the emergency reason, it would be requested that the portable-type FPD is employed for the radiographing operation in the concerned radiographing room in which the portable-type FPD is not equipped in the normal situation, or the like. In that case, unless the correlating relationship between the portable-type FPD and the radiographing room is made to be changed, since the portable-type FPD is still correlated with the console installed in the radiographing room serving as the departure site, instead of the concerned radiographing room serving as the destination site, the radiographing subject (patient) resides in the wrong radiographing room, which is different from the correct radiographing room correlated to the console to be used for radiographing the subject. Accordingly, if the radiographing operation is conducted in the abovementioned state, the operation for acquiring the radiographing image cannot be actually achieved, and merely a wasted X-ray exposure would occur in vain.

In order to change the correlating relationship from that with the console installed in the radiographing room serving as the departure site to that with the other console installed in the other radiographing room serving as the destination site, the following method could be employed.

(1) The console information in both the console of the departure site and the other console of the destination site are established by using one of the both consoles through the wireless communication path.

(2) The portable-type FPD is equipped with a separate setting section for the setting change use, so as to use the separate setting section for the above purpose. For instance, a device for connecting the portable-type FPD with the console through wire communication, a wireless communication device other than that to be used for controlling operations, etc. can be cited as the abovementioned separate setting section. In addition, it is necessary for the operator to manually move the radiographing sensitivity information to be utilized for the image correction processing to the other console of the destination site through the network or by using a certain kind of recording medium. However, even in any one of the abovementioned methods, the operator should once conduct establishing operations by employing a certain kind of method through manual operations, and accordingly, there has been a problem that such the establishing operations are cumbersome for the operator.

SUMMARY OF THE INVENTION

To overcome the abovementioned drawbacks in conventional radiographic image capturing system, it is one of objects of the present invention to provide a radiographic image capturing system, in which a portable-type radiographic image detecting device provided with a wireless communication section is included and a correlation established between the FPD and the console can be easily changed.

Accordingly, at least one of the objects of the present invention can be attained by any one of the radiographic image capturing systems described as follows.

(1) According to a radiographic image capturing system reflecting an aspect of the present invention, the radiographic image capturing system, comprises: a radiation irradiating apparatus to emit radial rays so as to irradiate the radial rays onto a subject; a radiographic image detecting device, being portable, to detect radial rays penetrated through the subject so as to generate radiation image data based on the radial rays detected; a plurality of controlling terminal devices, each of which displays a radiation image represented by the radiation image data generated by the radiographic image detecting device, and which are coupled to each other through a network; a wireless communicating section to transmit the radiation image data acquired by the radiographic image detecting device in a wireless communication mode; a communication information attaching section to attach communication information to the radiation image data to be transmitted by the wireless communication section; an access point that is correlated in advance with corresponding one of the controlling terminal devices, and transfers the radiation image data, which is received by the wireless communication section in the wireless communication mode within a predetermined area of a radiographing room in which the radiation irradiating apparatus is installed, into the network; and a correlation controlling section that correlates the radiographic image detecting device with the corresponding one of the controlling terminal devices so as to establish a correlation establishment between them, based on the communication information attached to the radiation image data by the communication information attaching section.

(2) According to another aspect of the present invention, in the radiographic image capturing system recited in item 1, the communication information is communication routing information.

(3) According to another aspect of the present invention, the radiographic image capturing system recited in item 1, further comprises: a plurality of access points, each of which is said access point; and a plurality of routers, which are disposed in such a manner that the routers respectively correspond to the access points, to which network addresses being different from each other are allotted, respectively; wherein the communication information is network address information of the radiographic image detecting device.

(4) According to another aspect of the present invention, the radiographic image capturing system recited in any one of items 1-3, further comprises: a radio wave intensity measuring section to measure an intensity of radio wave received at the access point in the wireless communication mode; wherein the correlation controlling section correlates the radiographic image detecting device with the controlling terminal device, based on information in regard to the intensity of radio wave, which is measured by the radio wave intensity measuring section in the wireless communication mode between the radiographic image detecting device and the access point.

(5) According to another aspect of the present invention, the radiographic image capturing system recited in any one of items 1-4, further comprises: a radiographing sensitivity storage section to store radiographing sensitivity information being inherent to the radiographic image detecting device, therein; wherein an identifying ID is attached to the radiographic image detecting device, so as to apply image correction processing to the radiation image data generated by the radiographic image detecting device, based on the radiographing sensitivity information, which is stored in the radiographing sensitivity storage section, and which is correlated to the identifying ID of the radiographic image detecting device concerned.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which.

DETAILED DESCRIPTION OF THE PREFERRED EMBODIMENT

Referring to an embodiment, the present invention will be detailed in the following. The scope of the present invention is not limited to the embodiment described in the following.

Figure 1:
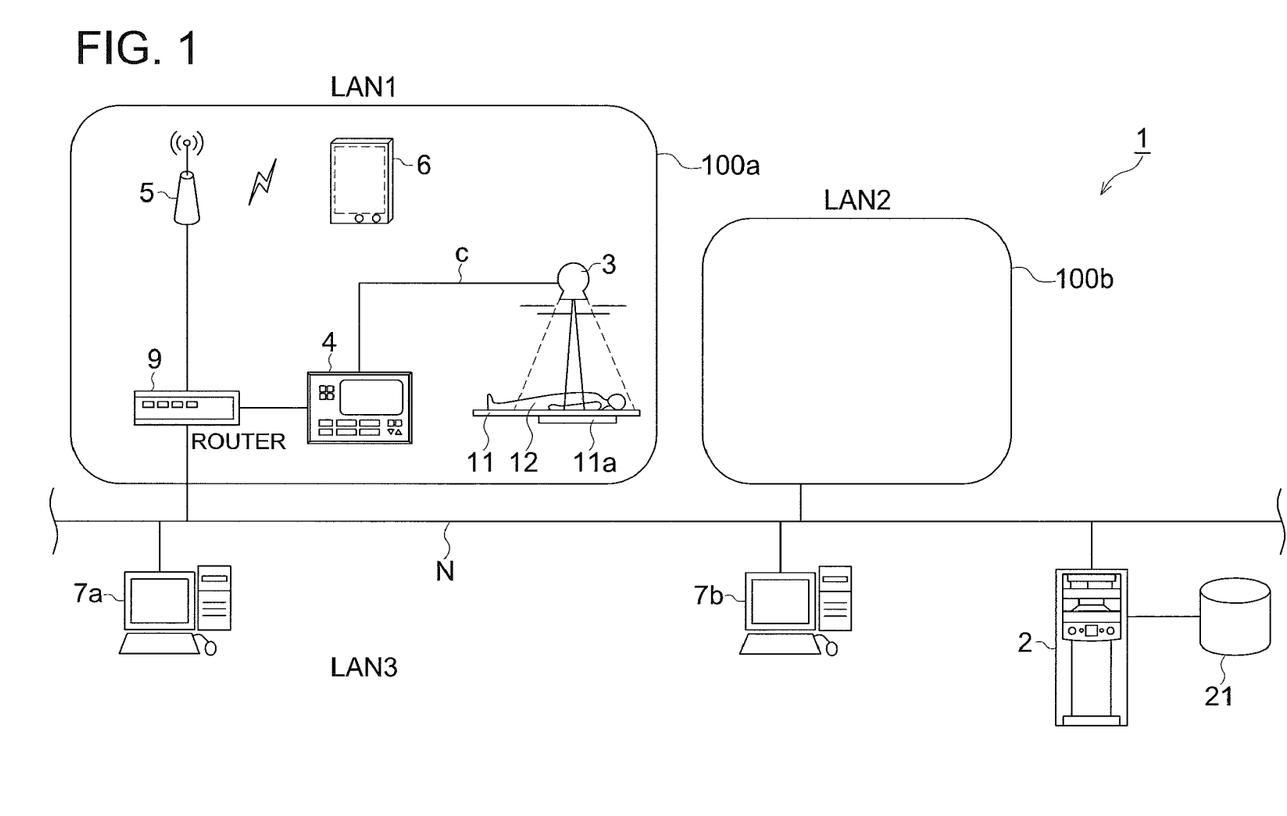
FIG. 1 shows a schematic diagram indicating a rough configuration of a radiographic image capturing system embodied in the present invention.

FIG. 1 shows a schematic diagram indicating a rough configuration of a radiographic image capturing system 1.

As shown in FIG. 1, the radiographic image capturing system 1 is constituted by a management server 2 to control various kinds of information in regard to the radiographing operation, a radiographing operation apparatus 4 to conduct various kinds of operations in regard to the radiographing operation, an access point 5 to perform a wireless communication by employing, for instance, a wireless LAN (Local Area Network), and a console 7 (serving as a controlling terminal device) to apply various kinds of image processing to radiation image data generated by a radiation image detecting device 6, all of which are coupled to each other through a network N. In this connection, the radiographic image capturing system 1 is also coupled to an HIS (Hospital Information System) serving as such a system that totally controls patient diagnosis information and accounting information, and a RIS (Radiology Information System) serving as such a system that controls information in regard to the radiographic medical care, through the network N, though those are not shown in the drawings. The network N may be an exclusive communication line to be used only for the radiographic image capturing system 1 concerned. However, due to the fact that the flexibility of the system would be deteriorated when the abovementioned exclusive communication line is employed, or from other reasons, it is preferable to employ an already-existing communication line, such as an Ethernet (Registered Trade Mark), etc.

Numerals 100a and 100b indicate radiographing rooms. Since internal layouts of the radiographing room 100a and the radiographing room 100b are substantially the same as each other, hereinafter, each of these radiographing rooms is simply referred to as a radiographing room 100, as a general term of them. The radiographing room 100 is provided with a radiation irradiating apparatus 3, the radiographing operation apparatus 4, the access point 5 for performing the wireless communication and a router 9 that is coupled to the access point 5. In this connection, the router 9 also serves as, for instance, a DHCP (Dynamic Host Configuration Protocol) server in conformity with the RFC1541.

By employing the router 9, a network equipped in the radiographing room 100a, another network equipped in the radiographing room 100b, and an internal network equipped within the concerned hospital constitute a LAN 1, a LAN 2 and a LAN 3, respectively, each serving as a sub-network.

A console 7a and a console 7b are correlated with an access point 5a provided in the radiographing room 100a and an access point 5b provided in the radiographing room 100b, respectively.

The radiation irradiating apparatus 3 is so constituted that radial rays are irradiated onto a patient 12 lying on a supine position radiographing bed 11 as a radiographing subject, and a detecting device insertion opening 11a, from which the radiation image detecting device 6 can be mounted, is disposed just below the supine position radiographing bed 11. Further, the system is so constituted that the radiographing operation apparatus 4 controls the radiation irradiating apparatus 3 so as to perform the radiographing operation under predetermined radiographing conditions. In this connection, it is applicable that the synchronization of the radiographing timing between the radiation irradiating apparatus 3 and the radiation image detecting device 6, mounted from the detecting device insertion opening 11a, is achieved by using the wireless communication through the access points 5 of them.

When the radiation image detecting device 6 and the console 7 communicates with each other in the wireless communication mode within a predetermined area of the radiographing room provided with the radiation irradiating apparatus 3, the access point 5 has a function for relaying the communication between them. In this connection, although an example, in which the wireless LAN (for instance, a communication method in conformity with the IEEE802.11a/b/f) is employed for the wireless communication, will be detailed in the following, the scope of the communication is not limited to the above. Other than the above-method employing the radio wave (spatial wave), it is also applicable to employ any one of various kinds of communication methods including an optical wireless communication method employing infrared rays, visible light, etc. (laser etc.) (for instance, IrDA), and an acoustic communication method employing acoustic waves or ultrasonic sound waves.

Further, each of the access points belongs to one of the sub-networks being different from each other, and is allotted with a corresponding one of the network addresses being different from each other. Still further, each of the access points is provided with a radio wave intensity measuring section (not shown in the drawings) that measures an intensity of radio wave received from the terminal device, such as the radiation image detecting device 6, so as to make it possible to transmit information in regard to the radio wave intensity to the terminal device concerned.

<Management Server>

The management server 2 is constituted by a computer, and is provided with a controlling section to control various kinds of sections included in the management server 2, an input operating section to input various kinds of information and user's instructions therefrom and a storage device to store various kinds of information therein (which are not shown in the drawings). In the embodiment of the present invention, the management server 2 serves as a "correlation controlling section". With respect to the correlation controlling operation, detailed descriptions will be provided later on.

A database 21 is coupled to the management server 2. The database 21 is serves as a "radiographing sensitivity storage section", so that the database 21 stores a radiographing sensitivity table, which is correlated with identifying IDs detailed later, and which serves as radiographing sensitivity information being inherent to each of the radiation image detecting devices 6. The radiographing sensitivity information, referred hereinafter, is defined as such information that includes positional information of a defect pixel whose sensitivity in respect to an incident energy is lower than a predetermined value or has a nonlinear characteristic, in addition to its gain and offset, when the incident energy is converted to the electric signals.

In this connection, in the explanations described in the foregoing, although the example in which the router 9 has the DHCP function has been described, it is also applicable that the management server 2 serves as the DHPC server instead of the router 9.

<Console>

Figure 2:
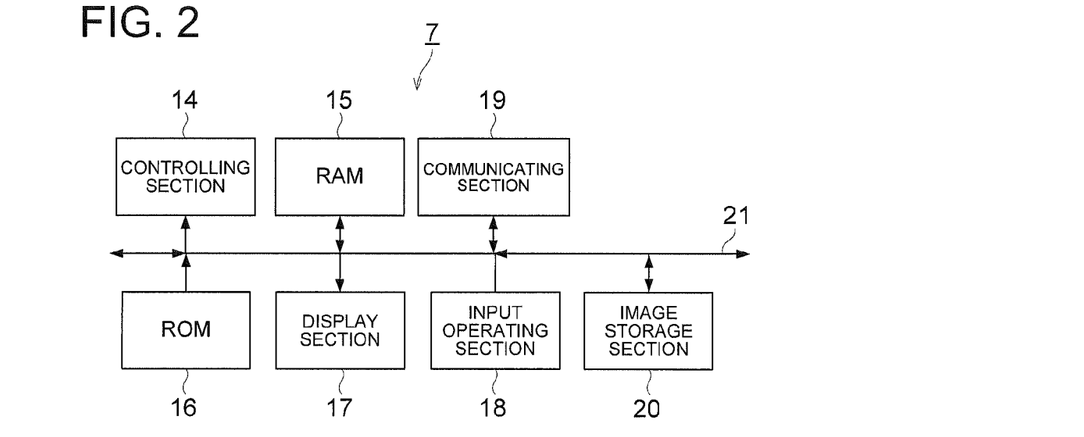
FIG. 2 shows a block diagram indicating a configuration of main sections included in a console.

FIG. 2 shows a block diagram indicating a configuration of main sections included in the console 7. As shown in FIG. 2, the console 7 is constituted by a controlling section 14, a RAM (Random Access Memory) 15, ROM (Read Only Memory) 16, a display section 17, an input operating section 18, a communicating section 19, an image storage section 20, etc., which are coupled to each other through a bus 22. In the present embodiment, a plurality of consoles 7a, 7b are coupled to the network N as aforementioned, and each of the consoles 7a, 7b is attached with, for instance, the console ID serving as identifying information for identifying the consoles 7a, 7b from each other.

The display section 17 is constituted by, for instance, a CRT (Cathode Ray Tube), a LCD (Liquid Crystal Display), etc., so as to display various kinds of display screens, such as a list of patients, various kinds of messages, etc., thereon, according to the instructions of the display signals sent from the controlling section 14.

The input operating section 18 is constituted by, for instance, a keyboard, a mouse, etc., so as to output a depression signal of a specific key, depressed by an operator from the keyboard, to the controlling section 14 as the inputted signal. In this connection, the input operating section 18 may be constituted by a so-called touch panel, a display screen of which is covered with a transparent sheet panel, so as to output positional information, representing a position onto which the operator's finger or an exclusive stylus touch pen is depressed by the operator concerned, to the controlling section 14 as the inputted signal.

Specifically, in the radiographic image capturing system 1 embodied in the present invention, it is applicable that the input operating section 18 is employed for inputting information of the patient to be radiographed, the radiographing information, etc., and displays the identifying ID of the radiation image detecting device 6, etc., when conducting the correlating operation, and further, is also employed for inputting an instruction for displaying a correlation confirming screen at that occasion. Hereinafter, the identifying ID is defined as identification information to be attached to the radiation image detecting device 6, so as to identify the concerned radiation image detecting device 6 from other devices.

The console 7 from which the identification information of the radiation image detecting device 6 is inputted, for instance, is a console 7 that corresponds to the radiographing room 100 in which the concerned radiation image detecting device 6 is installed. Although a position, at which the console 7 to control the radiographing room 100 should be installed, is not limited to a specific position, it is preferable that the console 7 is installed at such a position that is nearest to the radiographing room 100 or the radiographing operation apparatus 4. By fulfilling the abovementioned location, it becomes possible for the operator to operate the radiation image detecting device 6 from the position nearest to the radiographing room 100 or the radiographing operation apparatus 4, when the operator implements the radiographing operation of the patient 12.

Further, the patient information inputted from the input operating section 18 and the patient list created on the basis of the radiographing information are displayed on the display section 17, so that the patient to be radiographed and a region of the concerned patient to be radiographed are selectable from the patient list by using the input operating section 18. Still further, when plural radiation image detecting devices 6 correspond to the console 7 concerned, any one of the plural radiation image detecting devices 6, which is to be employed for actually radiographing the patient, is selectable by using the input operating section 18. According to the above, the operation for setting the specific radiation image detecting device 6, by which the patient is actually radiographed, is conducted. In this connection, it is also applicable that, when the abovementioned setting operation is once completed, the concerned information is transmitted to the management server 2, so that an instruction issued by the management server 2 bans the other console 7 from selecting the concerned patient on the patient list.

Still further, based on the predetermined operation, the input operating section 18 outputs signals in regard to the instruction for transferring the radiation image data, acquired as a detecting result detected by the radiation image detecting device 6, to the controlling section 14. In the present embodiment, the radiation image data acquired by the radiographing operation is transferred to such the console 7 that is correlated to the radiation image detecting device 6 actually used for the radiographing operation concerned and is used for operating the concerned radiation image detecting device 6 when the radiographing operation is implemented. Then, in the controlling section 14, the radiation image data concerned is correlated to the patient information and the radiographing information, etc., selected from the patient list at the time of the setting operation before the above radiographing operation is implemented. Finally, the radiation image data, correlated to the patient information and the radiographing information, etc., are stored into the image storage section 20 as needed, or transferred to an external device, such as the management server 2, etc.

Yet further, when the radiologist determines whether or not the subject image is appropriately captured (detected) by the radiation image detecting device 6 and whether or not the operation for re-radiographing the same subject is necessary, the radiologist inputs the above-determination results from the input operating section 18. Then, the input operating section 18 outputs the determination results inputted by the radiologist, to the controlling section 14 as electric signals.

The console 7 communicates with the network N through communicating section 19. Further, the console 7 communicate with the radiation image detecting device 6 in a wireless communication mode, such as wireless LAN (Local Area Network), etc., through the access point 5 coupled to the communicating section 19, so as to transmits and receives various kinds of information between them.

The controlling section 14 is constituted by a CPU (Central Processing Unit), etc., so as to develop various kinds of predetermined programs stored in the ROM 16 onto the working area provided in the RAM 15, and to implement various kinds of processing by executing the programs concerned.

<Radiation Image Detecting Device>

Figure 3:
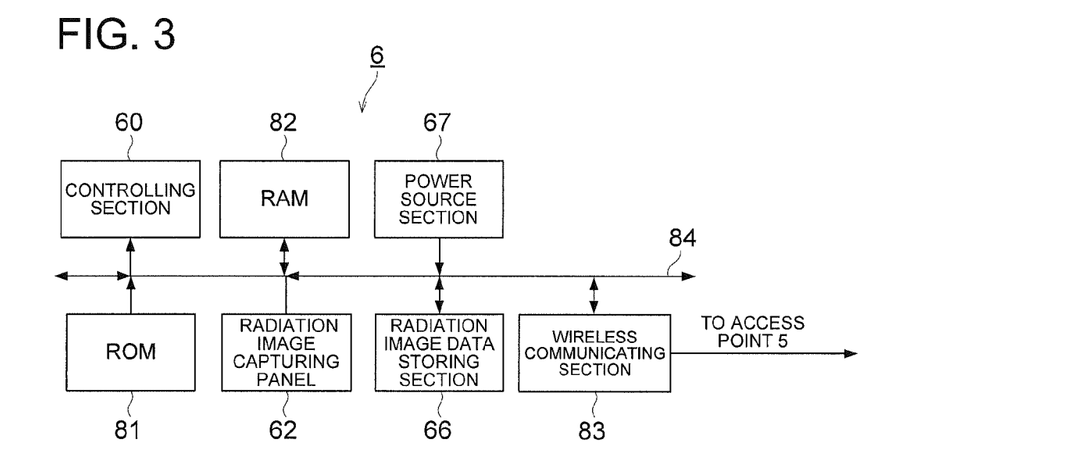
FIG. 3 shows a block diagram indicating a configuration of main sections included in a radiation image detecting device.

The radiation image detecting device 6 detects radial rays, which are irradiated from the radiation irradiating apparatus 3 and penetrated through the patient 12, so as to acquire radiation image data. The radiation image detecting device 6 is such a portable type cassette FPD device that accommodates a radiation image capturing panel called a FPD (Flat Panel Detector).

FIG. 3 shows a block diagram indicating a configuration of main sections included in the radiation image detecting device 6. As shown in FIG. 3, the control system of the radiation image detecting device 6 is provided with a controlling section 60, a radiation image capturing panel 62, a radiation image data storing section 66, a power source section 67, a ROM 81, a RAM 82, a communication section 83, etc., which are coupled to each other through a bus 84.

The controlling section 60 is constituted by a CPU (Central Processing Unit), etc., and reads out a control program stored in the ROM (Read Only Memory) 81, so as to develop the concerned program onto the working area provided in the RAM (Random Access Memory) 82, and to control various kinds of sections included in the radiation image detecting device 6 by executing the developed program.

The ROM 81 is constituted by a nonvolatile semiconductor storage device, etc., so as to serve as a "storage section" that stores the control program to be executed in the controlling section 60, various kinds of programs, address information of the management server 2 serving as the "correlation controlling section", the identifying IDs for identifying the FPDs from each other, etc.

The RAM 82 forms working areas that temporarily store the various kinds of programs being executable in the controlling section 60 and read out from the ROM 81, inputted data or data to be out putted, various kinds of parameters, etc., which are employed in various kinds of processing to be implemented and controlled by the controlling section 60.

The radiation image capturing panel 62, for instance, is provided with a glass plate substrate, at a predetermined area of which a plurality of detecting pixels are aligned in a matrix pattern. The plural detecting pixels aligned in a matrix pattern detect at least a part of radial rays, which are irradiated onto the patient 12 from the radiation irradiating apparatus 3 and penetrated through the patient 12, in response to intensity of the penetrated radial rays, and convert the detected radial rays to electric signals to be stored therein.

Incidentally, for instance, an indirect-type radiation image capturing panel that is provided with a radial-rays to light conversion layer to convert the radial rays to fluorescence (light) and a photoelectric conversion layer to detects the fluorescence converted by the radial-rays to light conversion layer so as to convert the detected fluorescence to electric signals, and a direct-type radiation image capturing panel that is provided with a radial-rays to electric-signal conversion layer having a radial rays accepting section to directly convert the radial rays to electric charges, instead of the radial-rays to light conversion layer and the photoelectric conversion layer, can be cited as the radiation image capturing panel 62, though those are not shown in the drawings. In this connection, indirect-type radiation image capturing panel is more preferable than the direct-type radiation image capturing panel, since a high-voltage power source to be employed in the direct-type is not necessary for the indirect-type.

The radiation image data storing section 66 is constituted by, for instance, a nonvolatile storage device, such as a Flash memory, etc., and a RAM, so as to make it possible to store radiation image data, which represent plural radiological images captured at plural times of image capturing operations and which are acquired by reading the electric signals stored in the radiation image capturing panel 62, therein.

The communication section 83 performs wireless communications of various kinds of information with the console 7 through the access point 5, by employing the wireless LAN (Local Area Network) in conformity with the IEEE802.11 standard.

The power source section 67 supplies electric power to a plurality of driving sections (including the controlling section 60, the radiation image capturing panel 62, the radiation image data storing section 66, etc.) that constitute the radiation image detecting device 6. The power source section 67 includes, for instance, a supplemental buttery and a rechargeable buttery, which can be charged by coupling a charging terminal to a cradle (not shown in the drawings).

<Correlation Controlling Operation 1>

Figure 4:
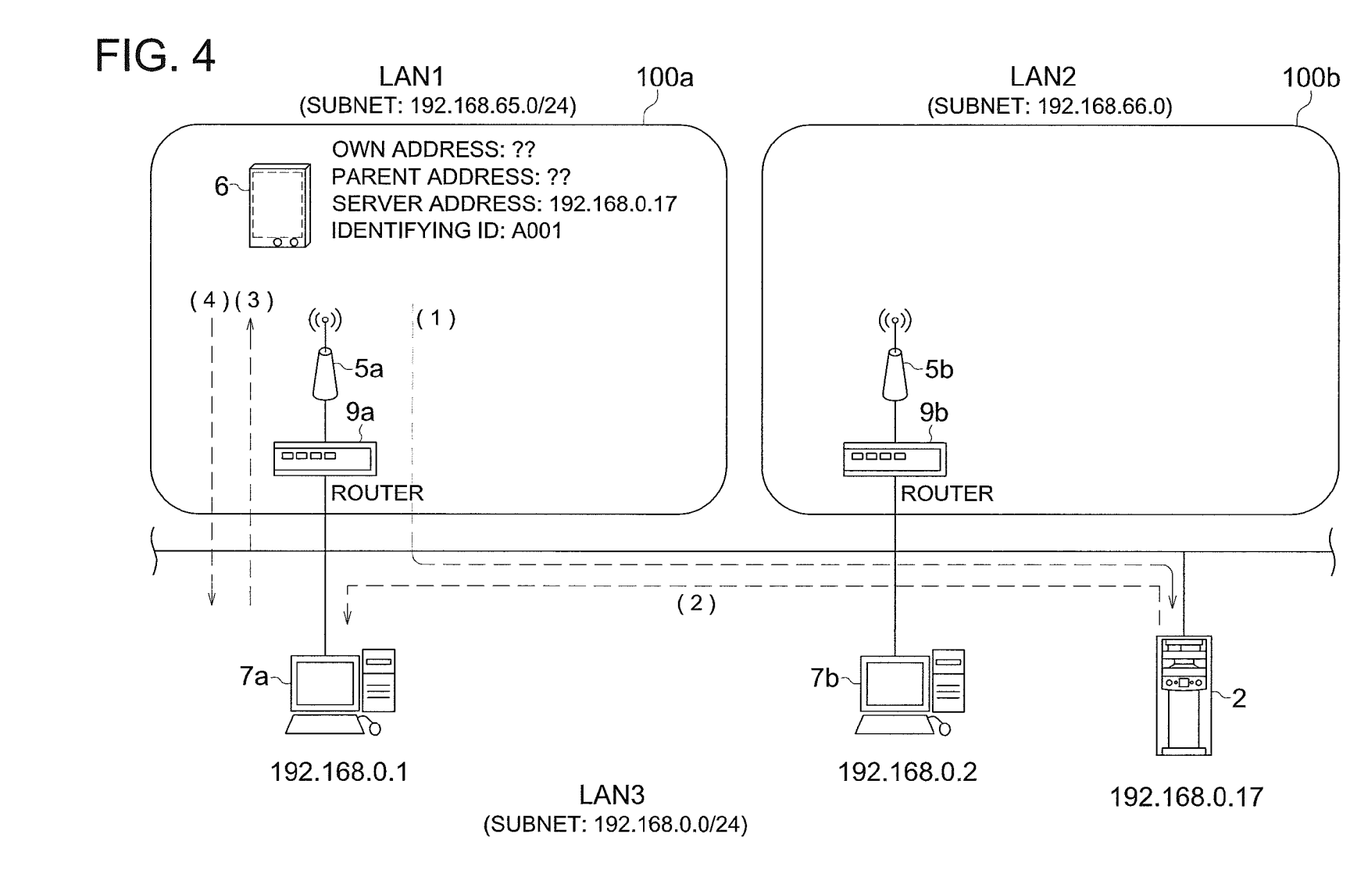
FIG. 4 shows an explanatory schematic diagram indicating a flow of data in a radiographic image capturing system embodied in the present invention.
Figure 5:
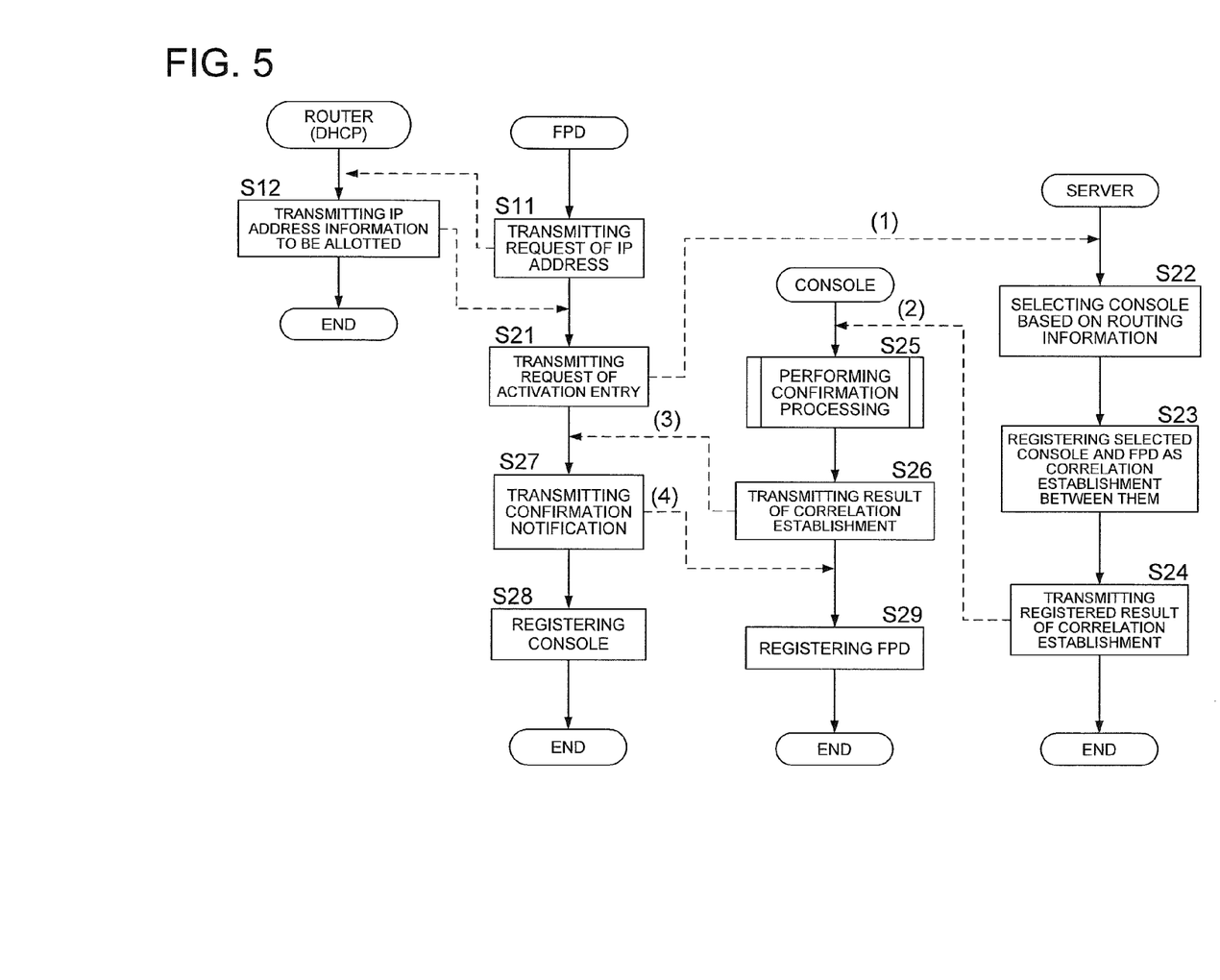
FIG. 5 shows an explanatory schematic diagram indicating a flow of controlling operations in a radiographic image capturing system embodied in the present invention.

Next, referring to FIG. 4 through FIG. 9, the operation for correlating the radiation image detecting device 6 (hereinafter, also referred to as the FPD) and the console 7 (controlling terminal device) with each other in the radiographic image capturing system 1 will be detailed in the following. FIG. 4 shows an explanatory schematic diagram indicating a flow of data in the radiographic image capturing system embodied in the present invention, while FIG. 5 shows an explanatory schematic diagram indicating a flow of controlling operations in the radiographic image capturing system embodied in the present invention. Incidentally, although FIG. 4 corresponds to FIG. 1, the constituents being unnecessary for explaining the controlling flow are omitted from the drawing.

After moving to the radiographing room 100, the operator turns ON the power source button to activate the FPD. As shown in FIG. 4, at the time of initial activated state, the IP address of its own (own address) and the address of the console to be correlated (parent address) with the own address is unknown. The other IP address (192.168.0.17) serving as the address information for the management server 2 and the identifying ID (A001) are store in advance in the ROM 81 serving as the storage section of the FPD. In this connection, it is also applicable that the MAC address attached to the communication section 83 is employed as the identifying ID.

In Step S11 shown in FIG. 5, when the operator depresses the button equipped on the FPD concerned, or when a certain kind of trigger signal is given by employing a timer or the like, a request of the IP address is transmitted to the DHCP server through the access point 5a of the wireless LAN. Receiving the request, the router 9a serving as the DHCP server transmits the IP address to be allotted to the FPD concerned (Step S12). In this connection, the IP address to be allotted is such an IP address that belongs to the subnet of the LAN1, for instance, 192.168.65.1.

Receiving the IP address to be allotted, the concerned FPD transmits a request of activation entry to the management server 2 by employing the IP address stored in the ROM 81 as the address information (Step S21, broken line (1) shown in FIG. 4). On that occasion, the IP address of the FPD, serving as the sender's IP address, and the routing information, namely the IP address of the access point 5a and the router 9a, are attached to the header information of the request of activation entry, arrived at the management server 2, by the router 9 that also serves as the communication information attaching section.

Referring to the header information included in the communication data, the management server 2, (1) based on the sender's IP address, identifies the subnet, or (2) based on the routing information, determines the router 9 through which the communication data has been transmitted, so as to find out the access point 5a through which the wireless communication with the concerned FPD has been actually implemented. Then, by finding out the access point 5a, the management server 2 selects the console 7a serving as the controlling terminal device that is correlated with the access point 5a concerned (Step S22).

The management server 2 registers the console 7a concerned and the FPD attached with the identifying ID (A001) into the storage section, while correlating them with each other as a correlation establishment between them (Step S23). In other words, the correlation establishment between the console and the FPD is to determine a specific console that receives the image data transmitted from one of FPDs. In this connection, hereinafter, with respect to a console and a FPD, which are in relationship of the correlation establishment, the concerned console is defined as a parent console for the FPD.

The management server 2 transmits the registered result of the correlation establishment to the console 7a serving as the parent console (Step S24, broken line (2) shown in FIG. 4). The information to be transmitted to the parent console includes the IP address and the identifying ID of the FPD correlated.

Figure 6:
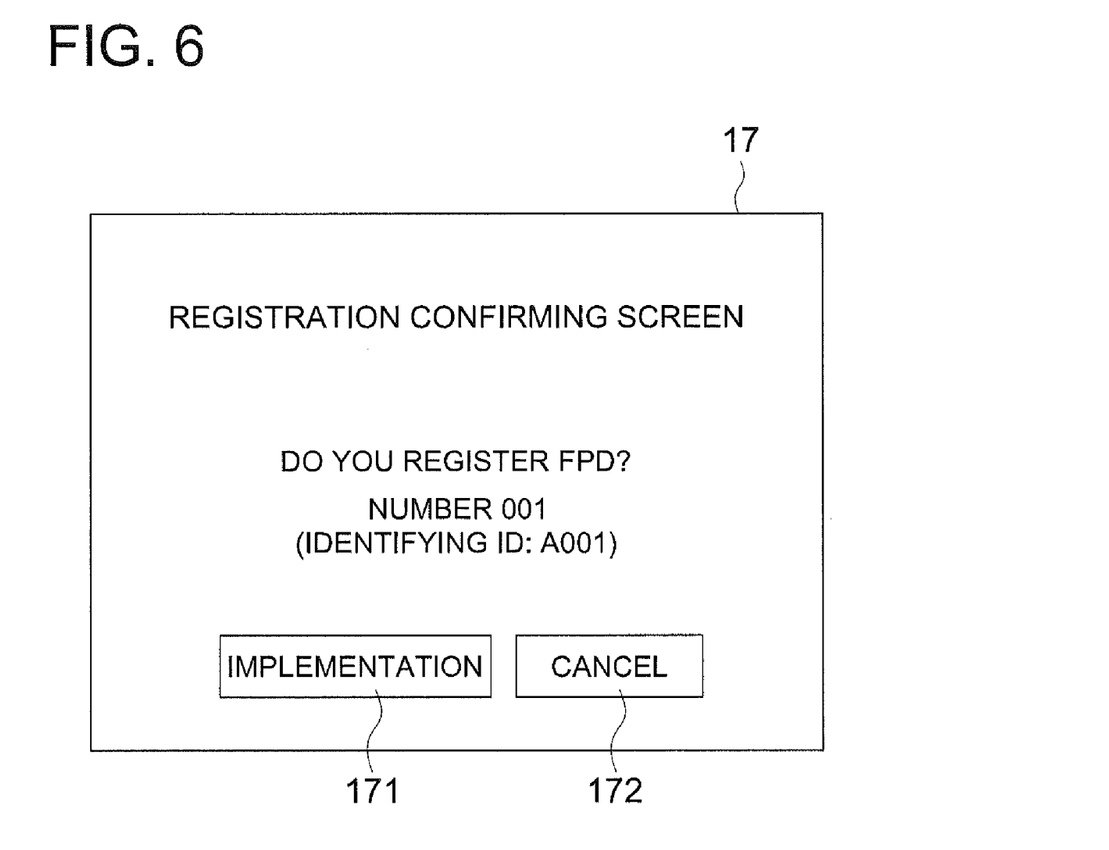
FIG. 6 shows a schematic diagram indicating a detailed screen layout to be displayed on a display section of a console.

The parent console performs a confirmation processing (Step S25). FIG. 6 shows a schematic diagram indicating a detailed screen layout to be displayed on the display section 17 of the console 7. As shown in FIG. 6, the parent console displays the information of the correlated FPD, which is received in Step S24, on the display section 17. The operator collates the identifying ID displayed on the display section 17 with the number or the like written on the covering surface or the like of the FPD to be used, so as to determine whether or not the concerned FPD corresponds to one that is intended to register (correlation establishment). When implementing the registering operation, the operator depresses an implementation button 171 to proceed to a next step and following steps of the registering operation.

Successively, in Step S26, the controlling section 14 of the console stores the result of the correlation establishment, which was transmitted in Step S24, into the ROM 16, and at the same time, transmits the result of the correlation establishment to the FPD (broken line (3) shown in FIG. 4). Receiving the result of the correlation establishment, the controlling section 60 of the FPD stores the result of the correlation establishment into the ROM 81, and at the same time, sends a confirmation notification (Ack signal) back to the parent console (Step S27, broken line (4) shown in FIG. 4). As a result of the above-mentioned operations, the correlation establishment has registered into both the parent console and the FPD (Step S28, Step S29).

Figure 7:
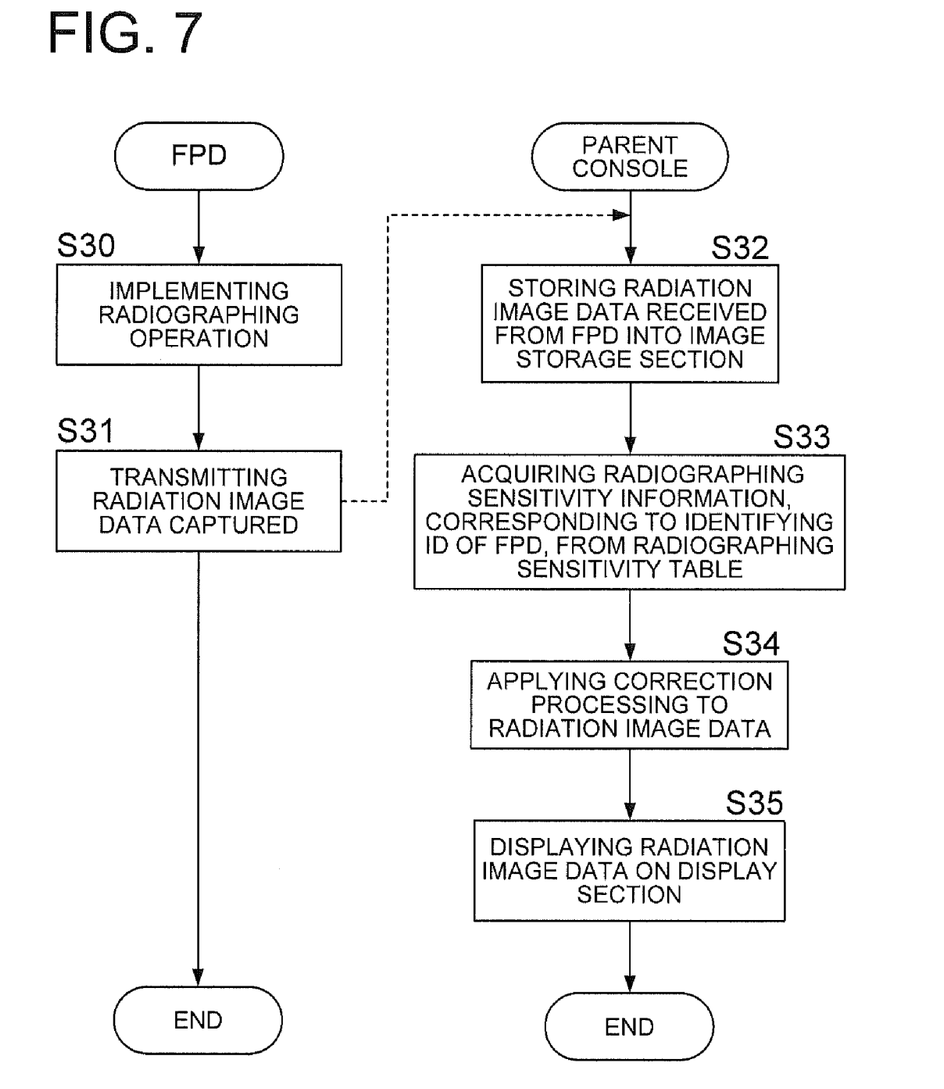
FIG. 7 shows an explanatory schematic diagram indicating a controlling flow in succession to the controlling flow shown in FIG. 5.

FIG. 7 shows an explanatory schematic diagram indicating a controlling flow in succession to the controlling flow shown in FIG. 5, namely, a controlling flow indicating a flow of a radiographing operation and radiation image data.

Initially, in Step S30, the radiographing operation is implemented. When implementing the radiographing operation, the operator selects a specific FPD to be used for the radiographing operation from FPDs registered in the parent console concerned. Then, the IP address of the selected FPD is transmitted to the radiographing operation apparatus 4 installed in the radiographing room 100 correlated to the parent console concerned. Since both the radiographing operation apparatus 4 and the FPD belong to the same subnet (for instance, LAN1), it is possible for both of them to directly communicate with each other. By performing the direct communications between them, the radiographing operation is implemented in such a manner that the timing for irradiating radial rays onto the subject from the radiation irradiating apparatus 3 is synchronized with the signal acquisition timing of the FPD concerned.

Successively, in the FPD, the radiation image data, acquired through the radiographing process, is temporarily stored into the radiation image data storing section 66. Then, after the consecutive radiographing operations have been completed, the radiation image data stored in the radiation image data storing section 66 are transmitted to the parent console correlated according to the controlling flow shown in FIG. 5 (Step S31).

Still successively, in the parent console, the radiation image data received from the FPD are stored into the image storage section 20 (Step S32). Then, the radiographing sensitivity information, corresponding to the identifying ID of the FPD used for the radiographing operation, is acquired as needed from the radiographing sensitivity table stored in the database (Step S33), so as to apply correction processing, such as a gain correction, an offset correction, etc., to the radiation image data concerned, based on the radiographing sensitivity information acquired in the above (Step S34).

Yet successively, the operator makes the display section 17 display the corrected radiation image data thereon, so as to confirm the result of the correction processing (Step S35), and then, further confirms that the radiographing operation has completed normally, to finalize the operation (END).

In this connection, when the console 7 and the FPD, which are correlated with each other in advance, communicate with each other, it is also applicable that a common key is allotted to both of them from the management server 2 or the like, so that the bilateral communications between them can be established by confirming the common key. According to the above-method, it becomes possible not to implement cryptographic communications between them, but also to prevent the FPD from being accessed from another console 7.

<Correlation Controlling Operation at the Time of Movement>

Figure 8:
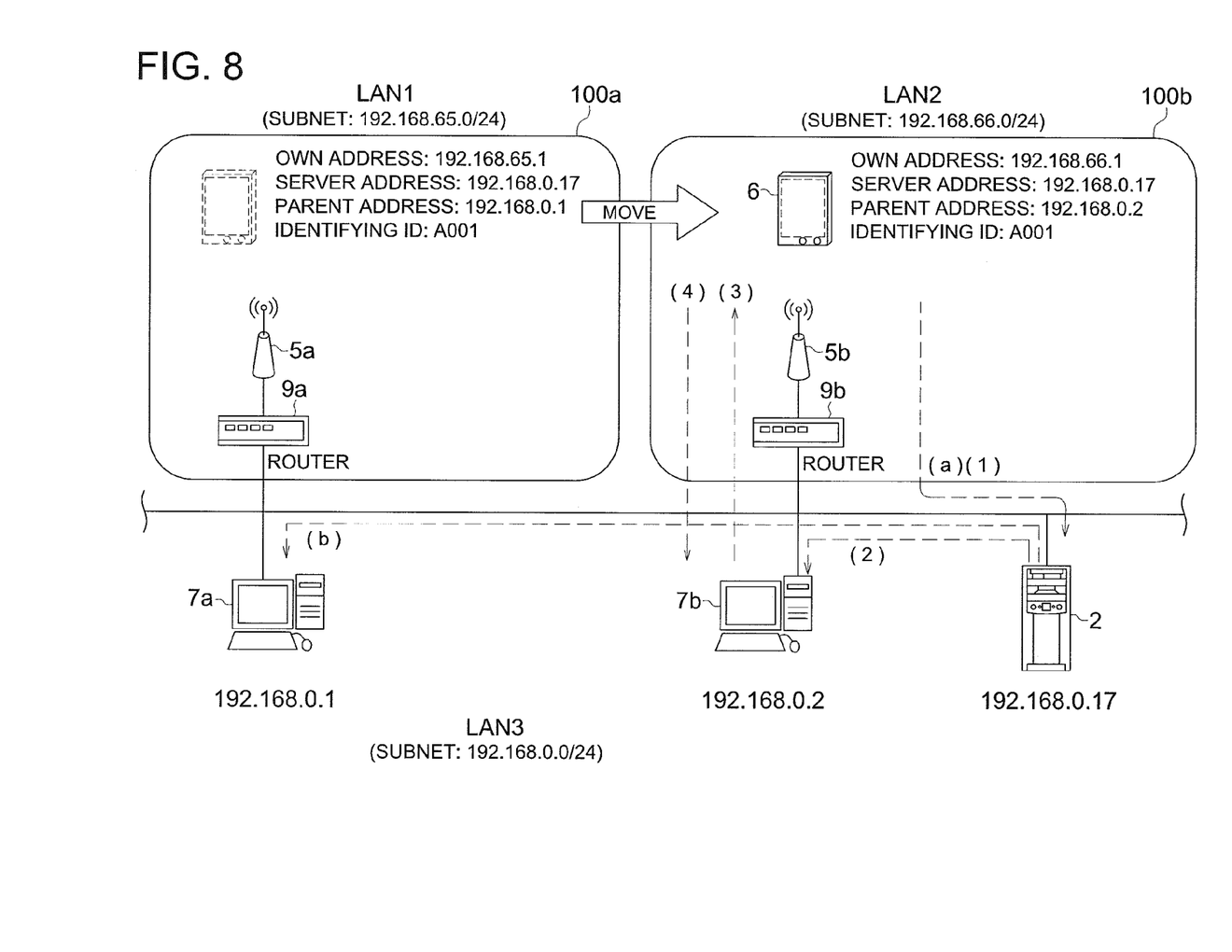
FIG. 8 shows an explanatory schematic diagram indicating a flow of data in a radiographic image capturing system embodied in the present invention.

Next, referring to FIG. 8 and FIG. 9, when the FPD is moved from the original radiographing room to another radiographing room while maintaining the correlation establishment with the original radiographing room in the power ON state, the correlation establishment with another console 7, installed in the other radiographing room serving as the moving destination, will be detailed in the following. FIG. 8 shows an explanatory schematic diagram indicating a flow of data in the radiographic image capturing system embodied in the present invention.

Figure 9:
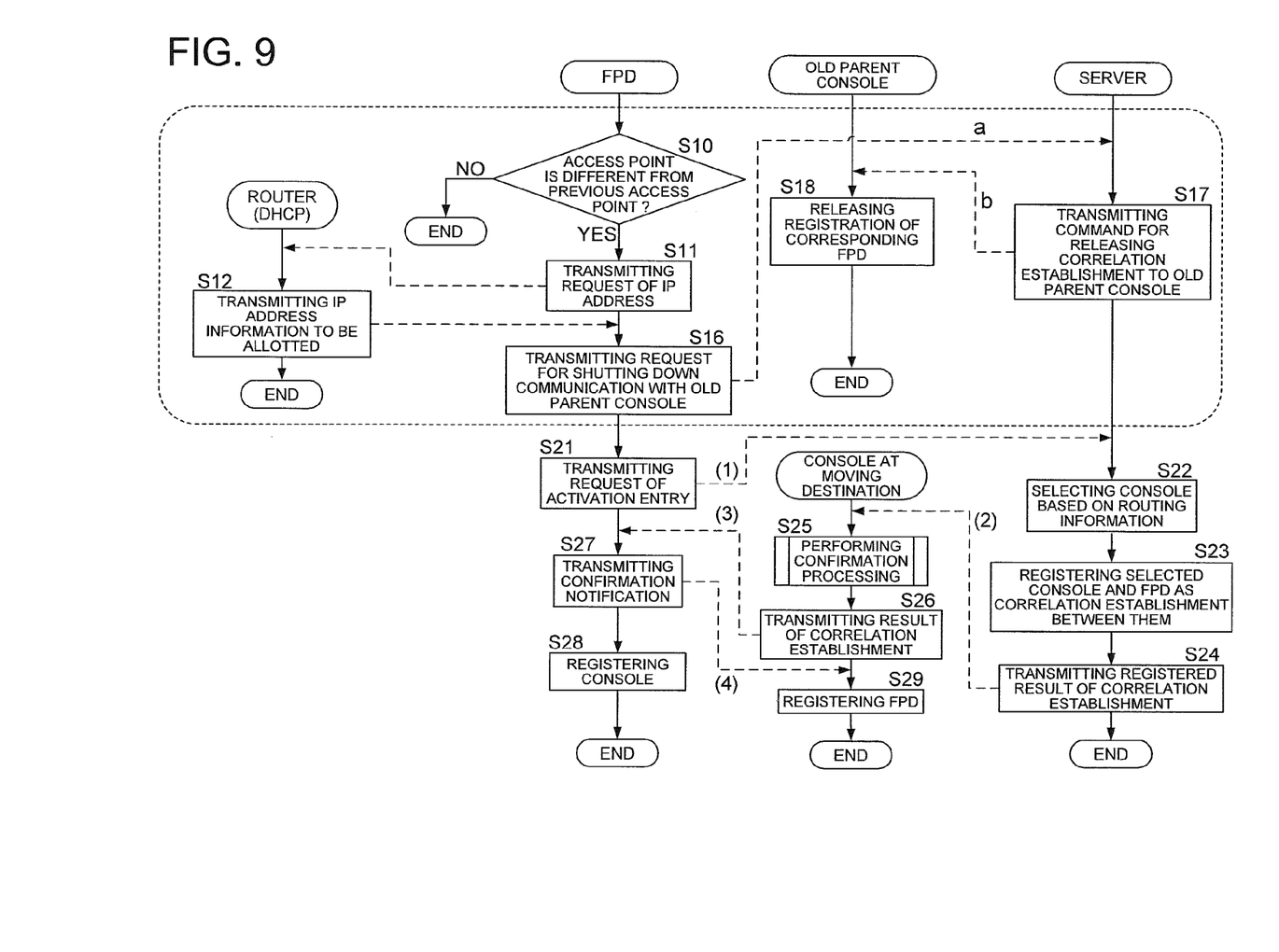
FIG. 9 shows an explanatory schematic diagram indicating a flow of controlling operations in a radiographic image capturing system embodied in the present invention.

FIG. 9 shows an explanatory schematic diagram indicating a flow of controlling operations in the radiographic image capturing system embodied in the present invention.

Referring to FIG. 8, when the FPD that has been originally installed in the radiographing room 100a is moved to the radiographing room 100b serving as the other radiographing room, the correlation establishment will be detailed in the following. Further, in the controlling flow shown in FIG. 9, since the operating steps having numbers equal to or higher than S21, other than the operating steps indicated in the area surrounded by the broken line, are the same as those shown in FIG. 5, explanations for them will be omitted.

In Step S10 shown in FIG. 9, the FPD determines whether or not the access point, through which the FPD is currently communicating, is different from the previous access point, through which the FPD communicated so far. In this connection, the FPD acquires information in regard to intensities of the radio waves at both the access point 5a being old before relocation and the access point 5b being new after relocation, respectively, and compares the acquired intensities with each other, so as to determine the access point to be affiliated at present. In this connection, the operation for acquiring the information in regard to the intensities of the radio waves is achieved by acquiring information detected by a radio wave intensity measuring section provided in each of the access points 5 in the FPD side.

When determining that the access point, through which the FPD is currently communicating, is different from the previous access point, through which the FPD communicated so far (Step S10; Yes), the FPD requests the DHCP server to allot a new IP address, so as to acquire the new IP address (Step S11).

After that, the FPD transmits a request for shutting down the communication with the console 7a to the management server 2, so as to eliminate the correlation establishment with the console 7a serving as the old console (Step S16, broken line (a) shown in FIG. 8). Receiving the request, the management server 2 specifies the old console, based on information for specifying the console 7, for instance, an IP address or a console ID, and then, transmits a command for releasing the correlation establishment with the concerned FPD to the console 7a specified in the above (Step S17, broken line (b) shown in FIG. 8).

Receiving the command for releasing the correlation establishment, the console 7a, being the old console, releases (deletes) the registration of the concerned FPD based on the identifying ID included in the command for releasing the correlation establishment (Step S18). Since the following steps are the same as those indicated in the controlling flow shown in FIG. 5, the explanations for them are omitted.

In this connection, it is also applicable that, at the time when the correlation establishment is completed, the console, which is installed in the relocated site, copies the radiographing sensitivity information from the management server 2 in advance as needed, prior to actual implementation of the radiographing operation, so as to makes it possible to speedily apply the image processing to the captured images at the time of actual radiographing operations.

Further, with respect to the case that the FPD is moved in a state of power OFF between the radiographing rooms, the flow of controlling operations can be explained according to the <CORRELATION CONTROLLING OPERATION 1> aforementioned.

In this connection, with respect to the operation for releasing the registration of the FPD (releasing the correlation establishment), although the embodiment, in which the releasing operation is conducted on the basis of the releasing request sent from the concerned FPD, has been exemplified in the foregoing, the scope of the present invention is not limited to the abovementioned embodiment. Any one of the following methods is also applicable for this purpose.

(1) When no periodical communication response is received from the FPD currently registered, the registration of the concerned FPD is released due to the timeout.

(2) When no response to the communication signal sent from the console is received from the FPD currently registered, the registration of the concerned FPD is released.

(3) When information, indicating that the intensity of radio wave communicated between the registered FPD and the access point (corresponding to the concerned console) is equal to or smaller than a predetermined intensity, is received, the registration of the concerned FPD is released.

(4) When the operator inputs the command for releasing the correlation establishment from the input operating section 18 of the console, the registration of the concerned FPD is released. Incidentally, in the above case, it is preferable that the command for releasing the correlation establishment is transmitted to the corresponding FPD.

As described in the foregoing, in a radiographic image capturing system that employs a portable type FPD provided with a wireless communicating section, by configuring the radiographic image capturing system so as to comply with the configurations and the flowcharts shown in FIG. 1 through FIG. 9, it becomes possible to obtain such the radiographic image capturing system that makes it possible to easily change the correlation establishment between the FPD and the console, when the concerned FDP is moved between the radiographing rooms being different from each other. Further, it also becomes possible to prevent the radiation image data, acquired by the radiographing operations, from being erroneously transmitted to an unintended console.

Further, according to the embodiment of the present invention, based on the sender's IP address or the routing information, the management server determines the specific router through which the communication data has been transmitted, so as to determine the radiographing room, in which the concerned FPD is currently used, by finding out the access point 5a through which the wireless communications with the concerned FPD have been actually implemented. Then, the management server selects, the console 7a correlated in advance to the concerned access point 5a, so as to establish the correlation between the concerned FPD and the console 7a. After that, the radiation image data acquired by using the concerned FPD is transmitted to the console 7a correlated in the above, namely, the console 7a being nearest to the radiographing room in which the concerned FPD is currently used. Therefore, it becomes possible to effectively perform the operation for confirming the radiation images after captured by the radiographing operations.

Still further, according to the embodiment of the present invention, the FPD acquires information in regard to intensities of the radio waves at both the access point 5a being old before relocation and the access point 5b being new after relocation, respectively, and compares the acquired intensities with each other, so as to determine the access point to be affiliated at present. Accordingly, the correlation establishing operation associating with the abovementioned can be easily achieved.

Still further, according to the embodiment of the present invention, since the radiographing sensitivity information corresponding to the identifying ID of the FPD used for the radiographing operations is acquired, and, based on the radiographing sensitivity information above-acquired, various kinds of correction processing, such as the gain correction processing, the offset correction processing, etc., is/are applied to the radiation image data, it becomes possible to acquire stable radiation image data without depending on various kinds of characteristic variations inherent to the FPD concerned.

According to the present invention, the following effects can be attained.

In the radiographic image capturing system that includes a portable-type radiographic image detecting device provided with a wireless communication section, it becomes possible to provide a radiographic image capturing system, which makes it possible to easily change a correlation established between the FPD and the console.

The invention claimed is:
1. A radiographic image capturing system, comprising:
a radiation irradiating apparatus to emit radial rays so as to irradiate the radial rays onto a subject;
a radiographic image detecting device, being portable, to detect radial rays penetrated through the subject so as to generate radiation image data based on the radial rays detected;
a plurality of controlling terminal devices, each of which displays a radiation image represented by the radiation image data generated by the radiographic image detecting device, and which are coupled to each other through a network;
a wireless communicating section to transmit the radiation image data acquired by the radiographic image detecting device in a wireless communication mode;
a communication information attaching section to attach communication information to the radiation image data to be transmitted by the wireless communication section;

an access point that is correlated in advance with corresponding one of the controlling terminal devices, and transfers the radiation image data, which is received by the wireless communication section in the wireless communication mode within a predetermined area of a radiographing room in which the radiation irradiating apparatus is installed, into the network; and a correlation controlling section that correlates the radiographic image detecting device with the corresponding one of the controlling terminal devices so as to establish a correlation establishment between them, based on the communication information attached to the radiation image data by the communication information attaching section, wherein the radiographic image capturing system, further comprise a radiographing sensitivity storage section to store radiographing sensitivity information being inherent to the radiographic image detecting device, therein; and wherein an identifying ID is attached to the radiographic image detecting device, so as to apply image correction processing to the radiation image data generated by the radiographic image detecting device, based on the radiographing sensitivity information, which is stored in the radiographing sensitivity storage section, and which is correlated to the identifying ID of the radiographic image detecting device concerned.

2. A radiographic image capturing system, comprising:

a radiographic image detecting device, formed in a portable-type, to acquire radiation image data based on radiation emitted from a radiation irradiating apparatus, and to transmit the radiation image data above-acquired in a wireless transmission mode;

an access point that is provided in a radiographing room in which the radiation irradiating apparatus is installed, so as to relay the radiation image data, which is transmitted from the radiographic image detecting device in the wireless transmission mode;

a plurality of controlling terminal devices, each of which receives the radiation image data transmitted from the radiographic image detecting device through the access point, and displays a radiation image represented by the radiation image data;

a management server that receives data transmitted from the radiographic image detecting device; and a communication information attaching device to attach communication information to the data, so as to generate communication-information attached data, which is to be transmitted to the management server through the access point;

wherein the management server receives the communication-information attached data sent from the radiographic image detecting device through the communication information attaching device, and selects a controlling terminal device from the plurality of controlling terminal devices, based on the communication information included in the communication-information attached data, currently received, and then, correlates the controlling terminal device, above-selected, with the radiographic image detecting device that has transmitted the communication-information attached data through the communication information attaching device, so as to output a correlation result concerned; and wherein the radiographic image detecting device acquires the correlation result outputted by the management server, and then, specifies a specific controlling terminal device to which the radiation image data is to be transmitted, based on the correlation result above-acquired.

3. The radiographic image capturing system of claim 2, wherein the management server transmits the correlation result to the controlling terminal device, above-selected; and wherein, receiving the correlation result, the controlling terminal device displays a registration confirming screen for confirming whether or not an operation for registering the radiographic image detecting device is necessary, based on the correlation result concerned.

4. The radiographic image capturing system of claim 3, wherein, when the registration confirming screen is operated for implementing the operation for registering the radiographic image detecting device, the controlling terminal device, which has received the correlation result, transmits the correlation result to the radiographic image detecting device concerned.

5. The radiographic image capturing system of claim 2, wherein the communication information is communication routing information.

6. The radiographic image capturing system of claim 2, wherein a wireless LAN (Local Area Network) communication mode is employed as the wireless transmission mode concerned, and a router is disposed at a position corresponding to the access point; and wherein, when the radiographic image capturing system is provided with a plurality of access points, network addresses, which are different from each other, are respectively allotted to the access points; and wherein the communication information is network address information.

* * * * *